(12) United States Patent
Kuchenbecker et al.

(10) Patent No.: US 10,456,318 B2
(45) Date of Patent: Oct. 29, 2019

(54) GAIT REHABILITATION SYSTEMS, METHODS, AND APPARATUSES THEREOF

(71) Applicants: THE TRUSTEES OF THE UNIVERSITY OF PENNSYLVANIA, Philadelphia, PA (US); The Research Foundation for The State University of New York, Albany, NY (US)

(72) Inventors: Katherine J. Kuchenbecker, Philadelphia, PA (US); Vivienne Clayton, Wayne, NJ (US); Ilana Teicher, Teaneck, NJ (US); Siyao Hu, Philadelphia, PA (US); Erin Vasudevan, Huntington Station, NY (US)

(73) Assignees: The Trustees of the University of Pennsylvania, Philadelphia, PA (US); The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 15/750,289

(22) PCT Filed: Aug. 5, 2016

(86) PCT No.: PCT/US2016/045705
§ 371 (c)(1),
(2) Date: Feb. 5, 2018

(87) PCT Pub. No.: WO2017/024201
PCT Pub. Date: Feb. 9, 2017

(65) Prior Publication Data
US 2018/0221239 A1    Aug. 9, 2018

Related U.S. Application Data

(60) Provisional application No. 62/201,799, filed on Aug. 6, 2015.

(51) Int. Cl.
*A61H 3/04* (2006.01)
*A61B 5/103* (2006.01)
(Continued)

(52) U.S. Cl.
CPC ............. *A61H 3/04* (2013.01); *A61B 5/1038* (2013.01); *A61B 5/112* (2013.01); *A61B 5/486* (2013.01);
(Continued)

(58) Field of Classification Search
CPC ...... A61H 3/04; A61H 3/008; A61H 2201/50; A61H 2201/1635; A61H 2201/5061;
(Continued)

(56) References Cited

U.S. PATENT DOCUMENTS

| | | | | |
|---|---|---|---|---|
| 2,730,266 A * | 1/1956 | Coursey | ................. | B44D 3/128 220/699 |
| 6,821,233 B1 * | 11/2004 | Colombo | .............. | A61F 5/0102 482/54 |

(Continued)

FOREIGN PATENT DOCUMENTS

EP    2730266 A1    5/2014

OTHER PUBLICATIONS

International Search Report and Written Opinion for International Application No. PCT/US2016/045705, dated Oct. 14, 2016—9 Pages.
(Continued)

*Primary Examiner* — Garrett K Atkinson
(74) *Attorney, Agent, or Firm* — Jenkins, Wilson, Taylor & Hunt P.A.

(57) ABSTRACT

Gait rehabilitation systems, methods, and apparatuses thereof are disclosed. In accordance with one aspect of the invention, a gait rehabilitation system may include a harness configured for attachment to an individual and at least one
(Continued)

sensor configured to sense at least one parameter associated with gait of an individual, the individual having an affected leg and an unaffected leg. The system includes a braking system configured for attachment to the harness and in communication with the at least one sensor. The braking system is further configured for monitoring the at least one sensor to sense the at least one parameter associated with an individual's gait, determining when the affected leg is in a modification portion of the individual's gait from the sensed at least one parameter, and applying a braking force resisting movement of the harness during the determined modification portion.

18 Claims, 9 Drawing Sheets

(51) Int. Cl.
| | | |
|---|---|---|
| *A61B 5/11* | (2006.01) | |
| *A61F 5/01* | (2006.01) | |
| *A61B 5/00* | (2006.01) | |
| *A61H 3/00* | (2006.01) | |
| *A61F 2/68* | (2006.01) | |

(52) U.S. Cl.
CPC .......... *A61B 5/4836* (2013.01); *A61F 5/0102* (2013.01); *A61H 3/008* (2013.01); *A61B 2505/09* (2013.01); *A61F 2/68* (2013.01); *A61F 2005/0169* (2013.01); *A61H 2003/043* (2013.01); *A61H 2003/046* (2013.01); *A61H 2201/0192* (2013.01); *A61H 2201/1635* (2013.01); *A61H 2201/1652* (2013.01); *A61H 2201/50* (2013.01); *A61H 2201/5061* (2013.01); *A61H 2201/5071* (2013.01); *A61H 2201/5084* (2013.01); *A61H 2201/5092* (2013.01); *A61H 2201/5097* (2013.01)

(58) Field of Classification Search
CPC ...... A61H 2201/0192; A61H 2003/046; A61H 2003/043; A61H 2201/1652; A61H 2201/5071; A61H 2201/5084; A61H 2201/5092; A61H 2201/5097; A61B 5/4836; A61B 5/1038; A61B 5/112; A61B 5/486; A61B 2505/09; A61F 5/0102; A61F 2/68; A61F 2005/0169
See application file for complete search history.

(56) References Cited

U.S. PATENT DOCUMENTS

| | | | | |
|---|---|---|---|---|
| 7,938,756 | B2* | 5/2011 | Rodetsky | A61H 1/0262 |
| | | | | 135/67 |
| 8,920,347 | B2* | 12/2014 | Bayerlein | A63B 22/0235 |
| | | | | 601/35 |
| 8,945,028 | B2* | 2/2015 | Kazerooni | A61H 3/00 |
| | | | | 601/35 |
| 9,914,003 | B2* | 3/2018 | Kuehne | A63B 69/0064 |
| 10,022,287 | B2* | 7/2018 | Shimada | A61H 3/00 |
| 10,039,684 | B2* | 8/2018 | Meuleman | A61H 1/0237 |
| 10,045,904 | B2* | 8/2018 | Takashima | A61H 1/0262 |
| 10,052,047 | B2* | 8/2018 | Feger | A63B 21/4045 |
| 10,052,252 | B2* | 8/2018 | Lin | A61H 1/0237 |
| 2003/0093021 | A1* | 5/2003 | Goffer | A61F 5/0102 |
| | | | | 602/23 |
| 2008/0255488 | A1* | 10/2008 | Agrawal | A63B 21/00181 |
| | | | | 602/23 |
| 2008/0287268 | A1* | 11/2008 | Hidler | A61H 3/008 |
| | | | | 482/69 |
| 2009/0298653 | A1* | 12/2009 | Rodetsky | A61H 3/04 |
| | | | | 482/69 |
| 2010/0152629 | A1* | 6/2010 | Haas, Jr. | A61B 5/1038 |
| | | | | 601/34 |

OTHER PUBLICATIONS

International Preliminary Report on Patentability for International Application No. PCT/US2016/045705, dated Feb. 15, 2018, 9 pages.

* cited by examiner though the following description pertains to an individual having suffered a stroke, aspects of the invention apply to individuals having various other conditions (e.g., traumatic brain injury, cerebral palsy, Parkinson's disease, an incomplete spinal cord injury, an orthopedic injury, an amputation, etc.) that result in gait abnormalities.

GAIT REHABILITATION SYSTEMS, METHODS, AND APPARATUSES THEREOF

CROSS-REFERENCE TO RELATED APPLICATION

This application is a U.S. National Phase filing of International Application PCT/US2016/045705, filed Aug. 5, 2016, and claims the benefit of U.S. Provisional Application No. 62/201,799, filed Aug. 6, 2015, the contents of each of which are incorporated herein by reference in their entireties for all purposes.

FEDERALLY SPONSORED RESEARCH STATEMENT

This invention was made with government support under contract number 0915560 awarded by the National Science Foundation. The government has certain rights in this invention.

FIELD OF THE INVENTION

The invention relates to systems and methods for rehabilitation and, more particularly, to systems, methods, and apparatuses relating to the rehabilitation of an individual's gait.

BACKGROUND OF THE INVENTION

Approximately 6.8 million adults in the United States of America have had a stroke, with a projected additional 3.4 million more by the year of 2030. Mobility impairments are a frequent cause of stroke-related disability: among ischemic stroke survivors 65 years and older, about half reported hemiparesis (weakness on one side) persisting six months post-stroke, and about 30% were unable to walk without assistance. With individuals living longer, a trend that is expected to continue as medical treatment improves and lifespans increase, the number of individuals suffering from mobility impairments will continue to increase over the years.

In addition, difficulty with functional movements, e.g., an individual's gait, can lead to physical deconditioning and less activity, which contributes to poor cardiovascular fitness, muscular atrophy, and metabolic syndrome. These effects, in turn, can increase the risk of a second stroke or cardiovascular event. In view of the foregoing, there is a need for effective methods and systems for gait rehabilitation.

SUMMARY OF THE INVENTION

Aspects of the invention include gait rehabilitation systems, methods, and apparatuses thereof.

In accordance with one aspect, the invention provides a gait rehabilitation method including sensing at least one parameter associated with a gait of an individual, the individual having an affected leg and an unaffected leg; determining when the affected leg is in a modification portion of the individual's gait from the sensed at least one parameter; and applying a braking force resisting forward movement of the individual during the determined modification portion.

In accordance with another aspect, the invention provides a gait rehabilitation system. The system includes a harness configured for attachment to an individual and at least one sensor configured to sense at least one parameter associated with gait of an individual, the individual having an affected leg and an unaffected leg. The system includes a braking system configured for attachment to the harness and in communication with the at least one sensor. The braking system further configured for monitoring the at least one sensor to sense the at least one parameter associated with an individual's gait, determining when the affected leg is in a modification portion of the individual's gait from the sensed at least one parameter, and applying a braking force resisting movement of the harness during the determined modification portion.

BRIEF DESCRIPTION OF THE DRAWINGS

The invention is best understood from the following detailed description when read in connection with the accompanying drawings, with like elements having the same reference numerals. When a plurality of similar elements is present, a single reference numeral may be assigned to the plurality of similar elements with a small letter designation referring to specific elements. When referring to the elements collectively or to a non-specific one or more of the elements, the small letters designation may be dropped. Included in the drawings are the following figures.

DETAILED DESCRIPTION OF THE INVENTION

Aspects of the present invention are directed to systems, methods, and apparatuses for gait rehabilitation. Adverse gait abnormalities often result from a leg being affected (e.g., a paretic leg) by an adverse medical condition or event such as a stroke. By improving the propulsion force of the affected leg, the adverse gait abnormalities may be reduced or cured.

Aspects of the present invention may be employed to strengthen, and thus, improve the propulsive force from an affected leg, promote symmetric propulsion from an individual's gait, provide better gait retention—and therefore, provide an overall superior gait rehabilitation. Systems and apparatus according to aspects of the invention may further enhance outpatient treatment and greatly reduce the overall cost associated with gait rehabilitation. Additionally, gait rehabilitation systems in accordance with aspects of the invention enable the individual to undergo rehabilitation on the ground, as opposed to on a treadmill or the like, which appears to provide improvements in cognitive responses post treatment.

Figure 1:
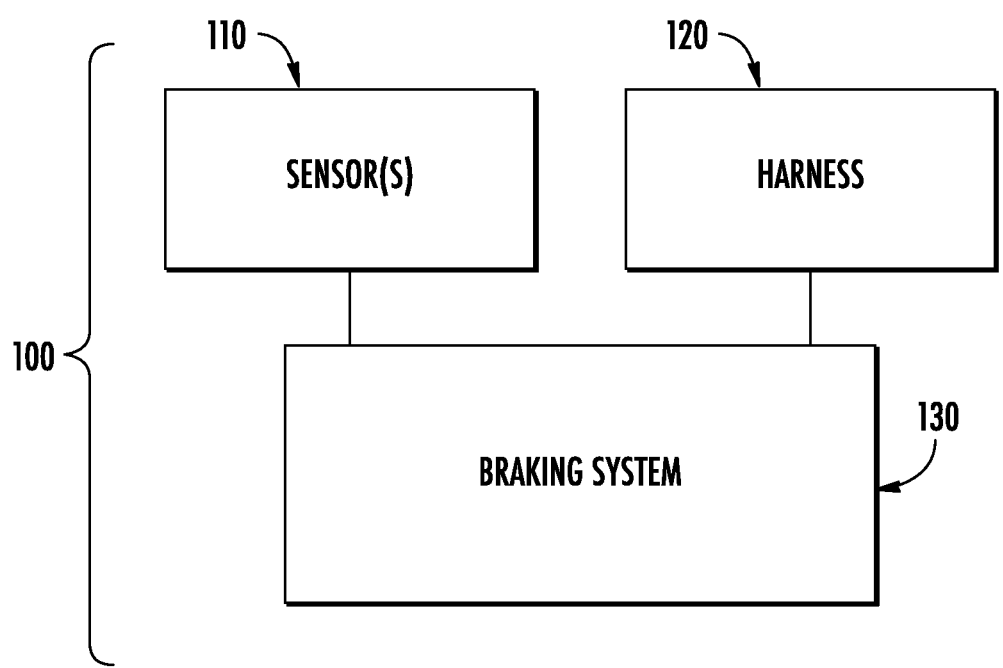
FIG. 1 is a schematic diagram of a gait rehabilitation system in accordance with aspects of the invention.

FIG. 1 depicts an exemplary gait rehabilitation system 100 in accordance with aspects of the invention. As a general overview, system 100 includes a harness 120, at least one sensor 110, and a braking system 130.

The harness 120 is configured to attach to an individual at a location that preferably facilitates the individual's ability to walk naturally. For example, harness 120 may be affixed to the individual's torso, waist, hips, and/or upper legs. In one embodiment, harness 120 is affixed to a lower region of an individual's torso, e.g., the individual's waist/pelvic region. Harness 120 may also be affixed at a location that corresponds to the individual's center of gravity, at a location that provides improved comfort, and/or avoids areas affected by other medical conditions.

The sensor(s) 110 are configured to sense at least one parameter associated with gait of an individual, and desirably, provide information for use in determining one or more phases of an individual's gait. Parameters that may be utilized include contact force between the individual's foot and a walking surface and/or movement of the individual's legs. Other parameters that may be used to determine one or more phases of the individual's gait will be understood by one skill in the art from the description herein. Suitable sensors for sensing the parameters associated with the individual's gait include, but are not limited to pressure sensors, force sensors, accelerometers, gyroscopes, magnetometers, inertial measurement units (IMUs), optical sensors, laser sensors, acoustic sensors, electromagnetic sensors, etc. Depending on the type of sensor, sensor(s) 110 may be affixed to the individual, e.g., attached to the affected and/or non-affected leg, or may be positioned elsewhere to facilitate sensing the desired parameter(s). In one embodiment, sensor(s) 110 sense parameter(s) solely from the affected leg. In another embodiment, sensor(s) 110 sense parameter(s) solely from the unaffected leg. In yet a further embodiment, sensor(s) 110 sense parameter(s) both the affected and unaffected leg.

Figure 2:
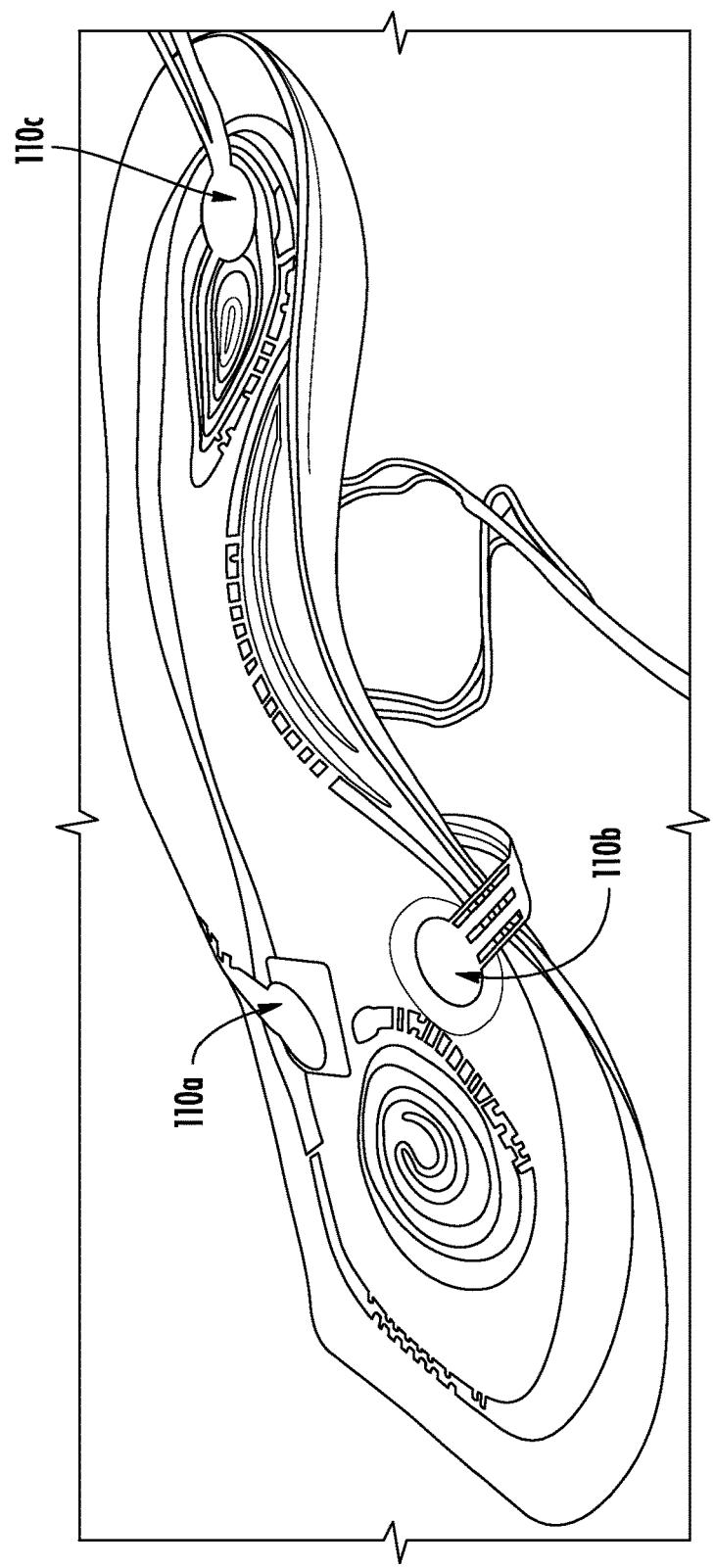
FIG. 2 is a perspective view of an implementation of the sensors of FIG. 1.

As illustrated in FIG. 2, sensor(s) 110 may be pressure sensors adapted to sense a force parameter applied to a walking surface by the weight of an individual. Although FIG. 2 shows three sensors 110a, 110b, and 110c, in other embodiments, system 100 may employ fewer or more sensors.

Desirably, sensor(s) 110 provide information for use in determining one or more phases of the individual's gait (or portions thereof). Sensor(s) 110 may include one or more sensor(s) 110a and/or 110b positioned near the front of an individual's foot that sense force/pressure from the front of the individual's foot and one or more sensor(s) 110c positioned near the back of an individual's foot that sense force/pressure from the back of the individual's foot. By sensing the weight distributed between a front and/or back portion of the individual's foot, sensor(s) 110 may supply information useful in determining one or more phases of the individual's gait (or portions thereof). In one embodiment, system 100 employs more than one type of sensor in conjunction with sensor(s) 110, e.g., a gyroscope may be utilize to sense rotation of the individual's foot.

The braking system 130 is configured to determine when an individual is in a modification portion of the individual's gait and to apply a braking force that resists movement of the individual during the determined modification portion of the individual's gait. The modification portion, as discussed later herein, includes one or more phases of an individual's gait (or portions thereof) during which systems and methods in accordance with aspects of the invention provide a braking force to the affected leg for use in rehabilitating the individual's gait. Braking system 130 is in communication with sensor(s) 110 and is configured to monitor sensor(s) 110 to sense parameter(s) associated with the individual's gait. Braking system 130 may be in communication with sensor(s) 110 by way of a wireless connection and/or wired connection. Based on the sensed parameter(s), braking system 130 may determine when the affected leg is entering a modification portion of the individual's gait and may apply a braking force in response to the sensed parameter(s). Braking system 130 may include a motor to provide a breaking force or, e.g., a base-line resistive force.

Figure 3A:
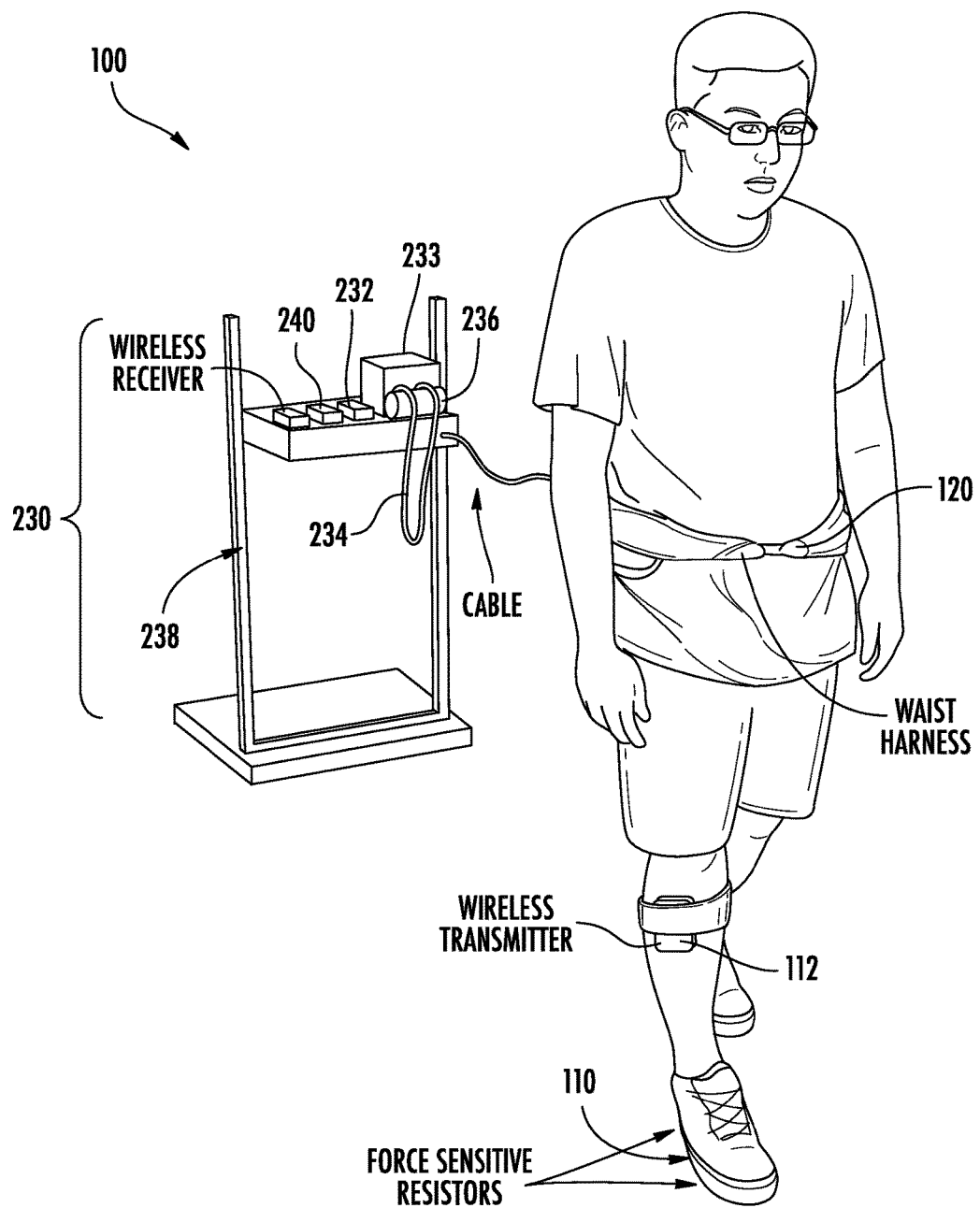
FIG. 3a illustrates an implementation of the gait rehabilitation system depicted in FIG. 1.
Figure 3B:
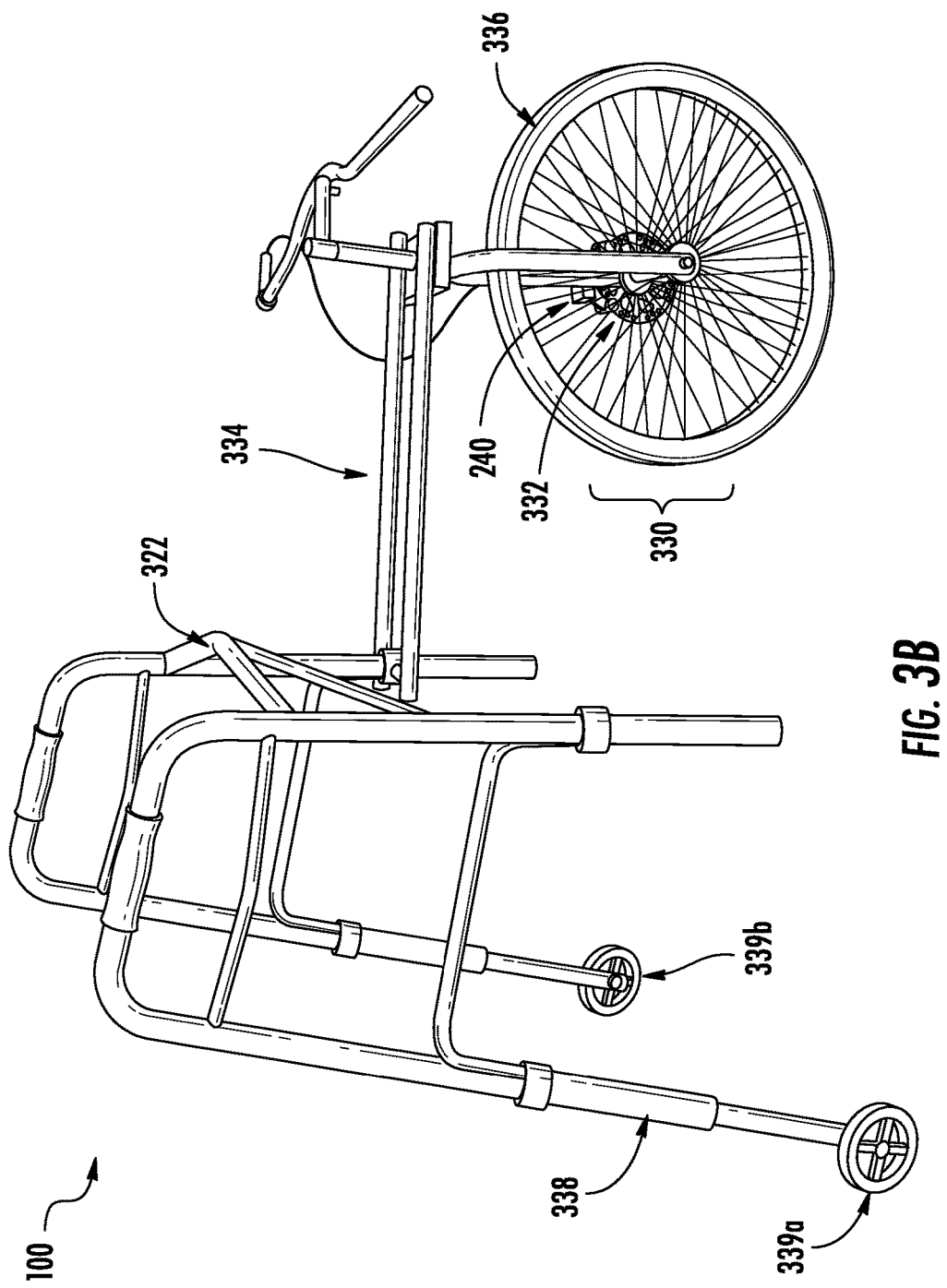
FIG. 3b illustrates another implementation of the gait rehabilitation system depicted in FIG. 1.

FIG. 3a shows one implementation of system 100 in accordance with aspects of the invention. The system 100 illustrated in FIG. 3a depicts a stationary gait rehabilitation system including harness 120, sensor(s) 110, and braking system 230. Although system 100 is configured in FIG. 3a to be stationary while in use, other implementations of system 100 may be mobile or portable during use, e.g., the implementation of system. 100 as illustrated in FIG. 3b.

The braking system 230 may include a tether 234, a brake 232, and a processor 240. Tether 234 is configured for attachment to harness 120 and may be of any suitable material, including one or more metals, polymers, natural fibers, or the like. In an exemplary embodiment, tether 234 includes a cable. Tether 234 may be coiled around a spool 236 prior to being doled out by braking system 230. Desirably, braking system 230 is coupled to a support structure 238 that enables tether 234 to be doled out at a set height, e.g., between 30 and 48 inches. In one embodiment, support structure 238 is configured such that brake system 230 is at about the same height as harness 120 when harness 120 is attached to the individual (e.g., around the waist or pelvic region). In another embodiment, tether 234 is substantially parallel to the ground when harness 120 is attached to the individual.

The processor 240 is configured to generate periodic braking signals, responsive to phases of the individual's gait. Processor 240 may receive and process the signals corresponding to one or more phases of the individual's gait, as sensed by sensor(s) 110. Alternatively, system 100 may employ a separate receiver that receives signals from sensor 110 and relays such signals to processor 240. A suitable processor is the M2 microcontroller board, which is available through the University of Pennsylvania. A suitable receiver is a mRF peripheral board, which is also available through the University of Pennsylvania.

The brake 232 is configured to periodically apply a braking force to the individual's movement. As the individual with attached harness 120 moves away from support structure 238, brake 232 doles out tether 234 while periodically applying a braking force to produce a resistive force against the individual's movement in response to the periodic braking signal. Brake 232 may be any suitable type of brake that provides adequate resistive force, e.g., by way of producing friction and/or a resistive torque on spool 236, which may create a force between brake 232 and tether 234. In one embodiment, brake 232 is a magnetorheological brake having a nearly linear relationship between the magnitude of the signal and the braking force produced by brake 232.

Desirably, brake 232 is configured to produce various amounts of resistive force to the individual, such as essentially any amount of resistive force less than 50 lbs. In one embodiment, brake 232 is configured to apply a resistive force of between 5 and 50 lbs., during the determined modification portion. In another embodiment, brake 232 is configured to provide a maximum resistive force of 35 lbs. Desirably, brake 232 is configured to provide a ramped increase in the resistive force leading up to and/or during ingression of the modification portion, a substantially steady amount of braking resistive force (e.g., 35 lbs.) during the modification portion, a ramped decrease in the resistive force after and/or during egression the modification portion, and a substantially steady amount of base-line resistive force (e.g., 0-5 lbs., 0-1 lbs., 1-5 lbs., etc.) until the next modification portion. The rehabilitation resistive force, the base-line resistive force, and the ramped increase/decrease may be controlled based on various factors (e.g., weight of the individual, leg strength of the individual, stage of rehabilitation, etc.).

System 100 may have a motor 233 in addition and/or alternative to brake 232. Preferably, motor 233 is configured to automatically reel the doled out tether 234 after an individual completes the gait training and/or when the individual is walking back to system 100, which may be determined by system 100 based on the at least one sensed parameter. Motor 233 may be configured to reduce or increase the resistive force, such as the base-line resistive force, generated by the brake 232. In one embodiment, motor 233 and brake 232 provide a base-line resistive force that is below 1 lb.

FIG. 3b shows a portable implementation of system 100 that moves during use of system 100. As a general overview, system 100, as illustrated in FIG. 3b, includes a brake system 330 and a support structure 338 having a wheel 336. In the illustrated embodiment, the wheel 336 is coupled to the support structure by a level portion 334.

The support structure 338 is configured for attachment to harness 120 (FIG. 3a), by way of coupling and/or attachment of harness 120 to attachment point 322 of support structure 338. The individual's movement, while attached to harness 120, translates into movement of system 100. Desirably, support structure 338 has an adjustable height such that attachment point 322 is at approximately the same height as attached harness 120, e.g., at the height of the individual's pelvic region.

The support structure 338 is coupled to at least one wheel, e.g., wheel 336. Wheel 336 may support at least a portion of the support structure 338. Additional wheels such as wheel 339a and/or 339b may be employed by support structure 338 to provide balance and/or additional support to system 100. Wheel 336 is attached to brake system 330. Support structure 338 may be configured to have a level portion 334 that provides distance between wheel 336 and the individual. The level portion 334 may provide additional stability to support structure 338, e.g., by way of reducing vertical force applied by the individual to wheel 336 and/or by reducing the likelihood of system 100 tipping over at wheel 336. System 100 may be configured to enable an individual to walk on a walking surface, such as the ground during gait rehabilitation sessions. Desirably, system 100 is configured to be stable on uneven walking surface, such that gait rehabilitation sessions may be performed on non-flat ground.

The braking system 330 includes processor 240 and brake 332 configured to apply a resistive force to at least one wheel, e.g., wheel 336, in response to a braking signal generated by processor 240. As the individual moves support structure 338, brake 332 applies a braking force during the modification portion of the individual's gait, e.g., by producing friction between brake 332 and wheel 336, thereby producing a resisting force against the individual's movement in response to the braking signal. Brake 332 may be any suitable type of brake that provides adequate resistive force, e.g., by way of producing friction, a resistive torque, or the like between brake 232 and wheel 336.

Figure 4:
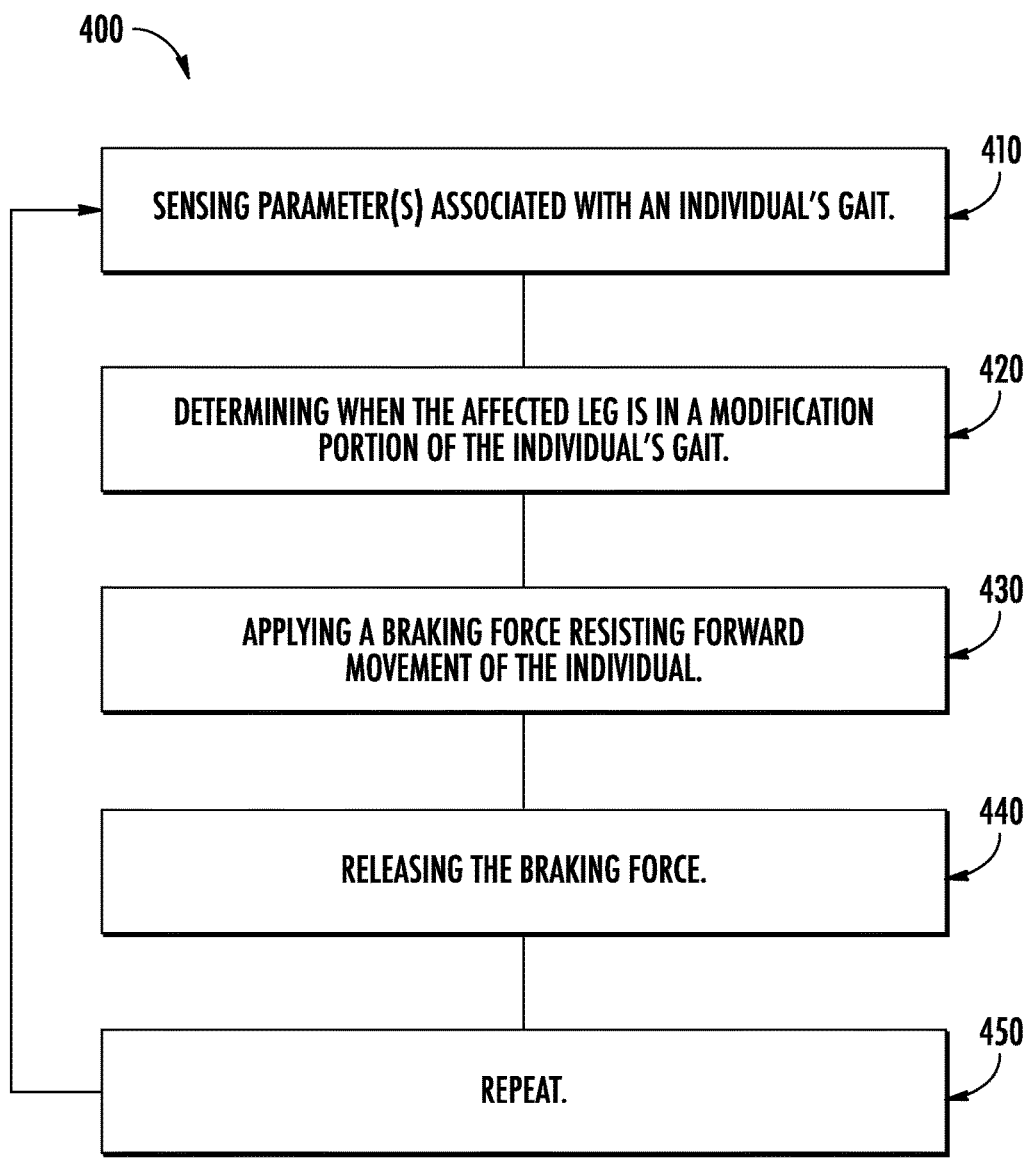
FIG. 4 is a flow chart depicting a method for gait rehabilitation according to aspects of the invention.

FIG. 4 illustrates an exemplary gait rehabilitation method 400. Method 400 is described with reference to gait rehabilitation system 100 for the sole purpose of facilitating description thereof. Other suitable systems will be understood by one of skill in the art from the description provided herein.

In step 410, at least one parameter associated with one or more phases of an individual's gait is sensed, e.g., by way of at least one sensor 110. Sensor(s) 110 may sense a parameter such as force and/or movement. For example, sensor(s) 110 may sense a foot of the unaffected leg contacting a walking surface, thereby providing useful information regarding the determination of whether the affected leg is in the modification portion. The placement of the sensor(s) 110 may depend on the type of sensor employed. In one embodiment, sensor(s) 110 sense the pressure exerted on a walking surface by an affected foot of the affected leg. In another embodiment, sensor(s) 110 sense pressure exerted on a walking surface by the unaffected foot of the non-affected leg. As another example, where an optical sensor is employed, step 310 may include sensing the movement or displacement of the affected and/or unaffected leg.

In step 420, the affected leg's presence in modification portion of the individual's gait is determined from the at least one sensed parameter. Without being limited to any particular theory, it is thought by the inventors that methods according to aspects of the invention described herein act upon the individual's gait, while in the modification portion, to promote superior gait rehabilitation by improving the propulsive force from the affected leg, promoting symmetric propulsion from an individual's gait, providing better gait retention, and improving muscle memory and/or cognitive abilities.

The modification portion may include one or more phases of an individual's gait (or portions thereof) depending on the specific gait abnormality and/or medical conditions. Accordingly, ingression, egression, and/or duration of the modification portion may be determined based on whether the affected leg and/or unaffected leg is in a swing phase, mid-stance, heel-off, terminal stance, foot flat, etc. For example, in step 420, method 400 may determine when the affected leg is entering and/or is in the modification portion by determining when a forward portion of the affected foot is on the walking surface, e.g., by sensing the flat foot, mid stance, or heel off phase. In another embodiment, the method determines when the affected leg is entering and/or is in the modification portion by determining when the heel of the affected leg is contacting the walking surface, e.g., heel strike phase. Method 400 may determine when the affected leg is entering the modification portion based on sensing when the unaffected foot is in or about to be in the air, e.g., by sensing the heel off, toe off, and/or mid-swing phases. In one embodiment, determination of when the affected leg is in the modification portion includes determining when a forward portion and/or a heel portion of the affected foot is on the walking surface and the unaffected foot is in the air. The determination of when the affected leg is entering the modification portion may also depend on the precision of equipment used to employ method 400, e.g., the accuracy of the sensors, speed and quality of the braking system, etc.

In steps 430 and 440, a braking force resisting forward movement of the individual is applied to the affected leg during the modification portion of the affected leg. As described in further detail herein with respect to FIG. 5, brake system 130 may apply a base-line level of resistive force (e.g., less than 1 lbs., 2 lbs., 3 lbs., 4 lbs., 5 lbs., etc.) that gradually increases (responsive to the affected leg entering and/or being in the modification portion) to a rehabilitation level of resistance (e.g., 35 lbs.) and gradually decreases (responsive to the affected leg leaving and/or not being in the modification portion) back to the base-line level of resistance. In one embodiment, wherein the individual wears a harness that is attached to brake 130 by tether 234, which is wound on spool 236 of brake 232, brake system 130 may apply a braking force by applying brake 232 to spool 236 to increase resistive force needed to unwind tether 234 from spool 236. In another embodiment, the individual is supported by a movable structure that has at least one wheel 336 and enables the individual to exert force with the affected leg on a walking surface, preferably the ground, while applying a braking force during the modifications portion of the affected leg by applying brake 332 to the at least one wheel 336 to increase resistive force needed to move the movable structure.

In step 450, method 400 is repeated in accordance with the individual's gait.

Figure 5:
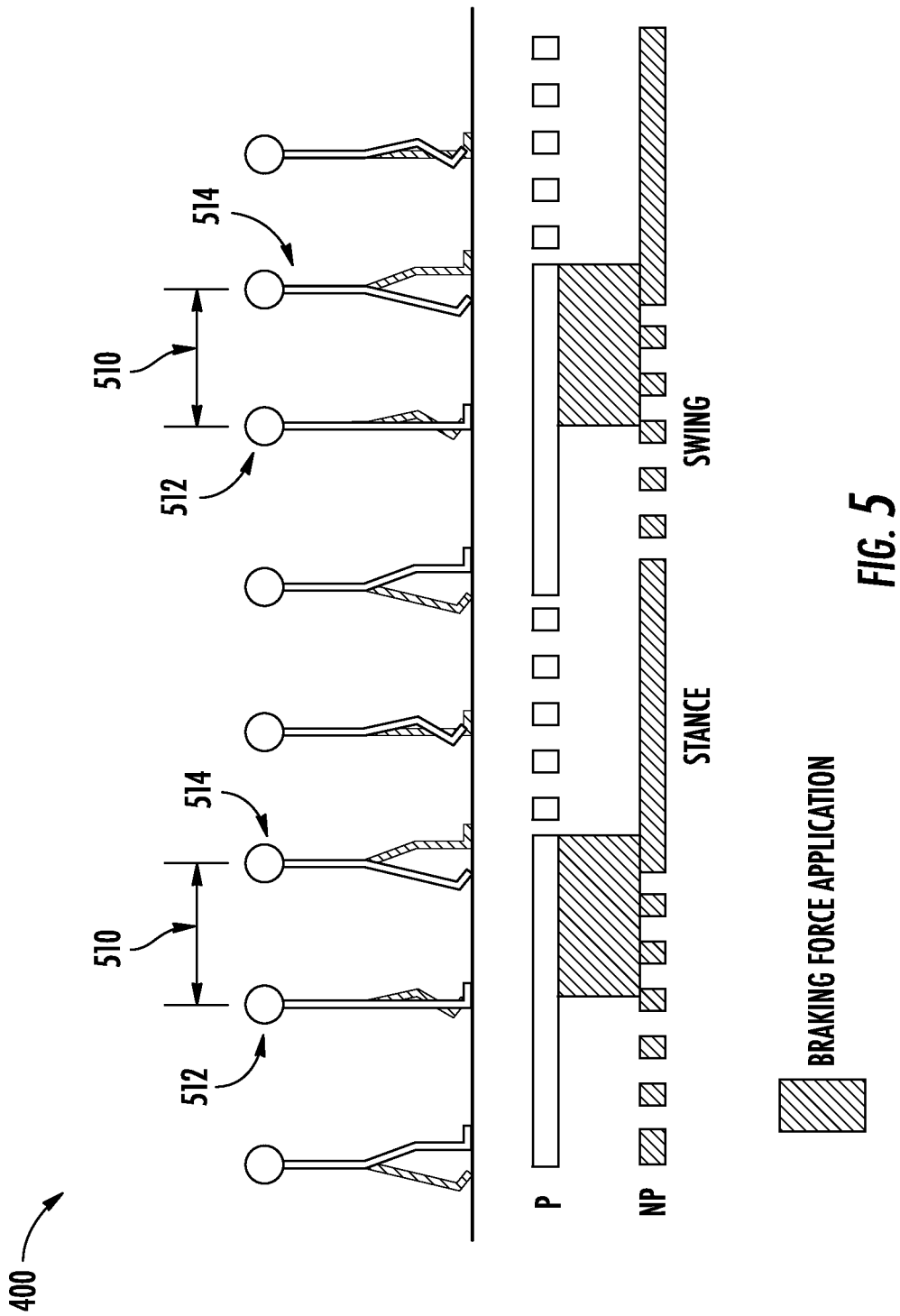
FIG. 5 is a schematic depicting a periodically applied braking force according to one embodiment of the method shown in FIG. 4.

FIG. 5 depicts an illustration of a braking force applied during modification portions 510 of one embodiment of method 400. In the illustrated example, each modification portion 510 spans the mid-stance phase 512 through terminal stance phase 514, e.g., the toe off phase of the affected leg. Prior to mid-stance phase 512, e.g., during the loading phase of the affected leg and/or during the swing phase of the unaffected leg, the resistive force applied to the individual may be gradually increased from a baseline tension (e.g., 0-1 lbs., 1-2 lbs., 2-3 lbs., 3-4 lbs., 4-5 lbs., etc.) to a full rehabilitation tension (e.g., approximately between 30 and 40 lbs.). During mid-stance 512 to terminal stance phase 514 of the individual's gait, the resistive force is maintained at full tension. Prior to and/or just after terminal stance phase 514, the resistive force is gradually decreased back to the base-line. This pattern is repeated on a periodic basis as the individual walks along the ground and/or walking surface.

Figure 8:
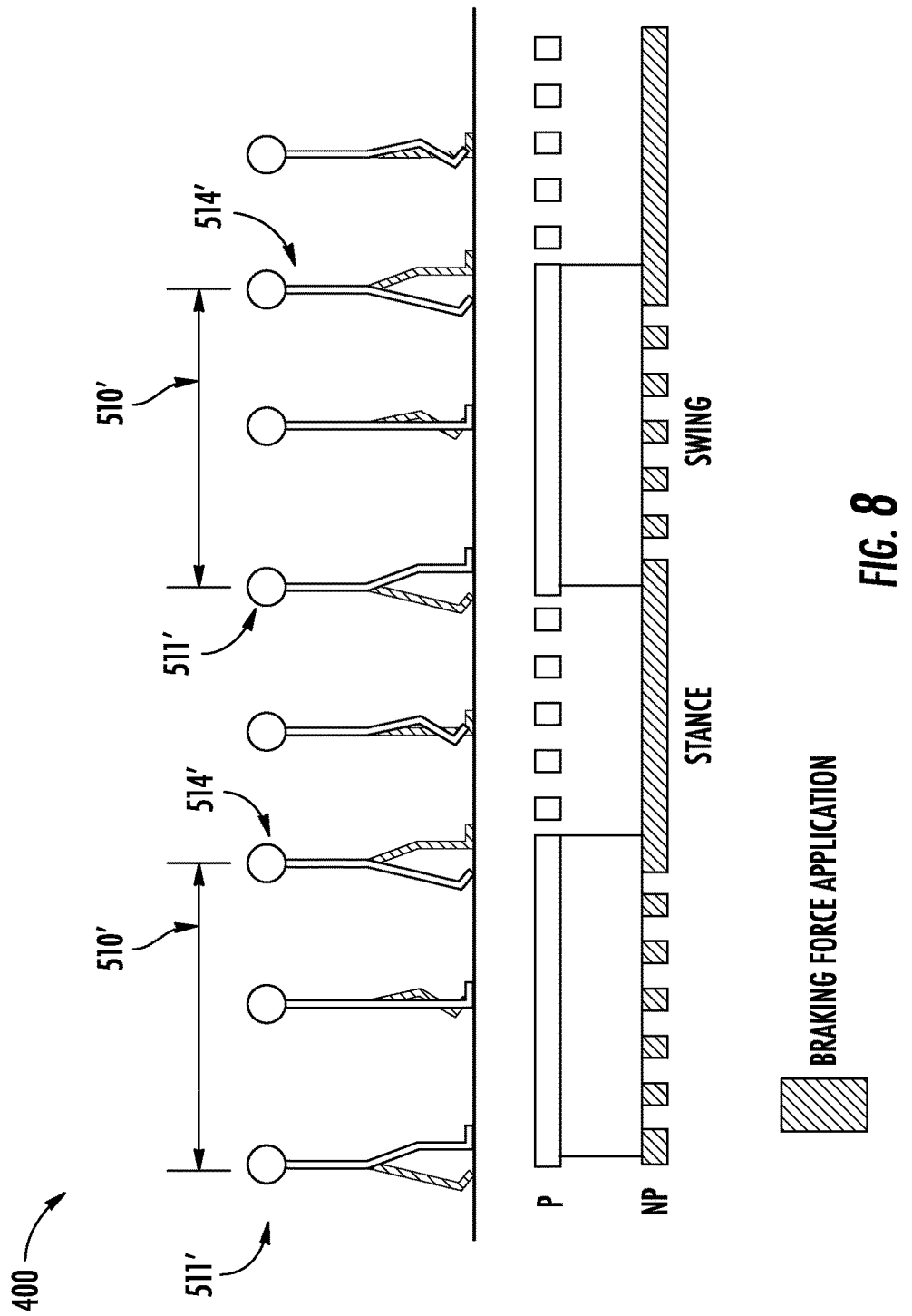
FIG. 8 is a schematic depicting a periodically applied braking force according to another embodiment of the method shown in FIG. 4.

FIG. 8 depicts an illustration of a braking force applied during modification portions 510' of another embodiment of method 400. In the illustrated example, each modification portion 510' spans from the heel of the affected foot contacting the walking surface 511', e.g., heel strike phase, through terminal stance phase 514' of the affected leg, e.g., the toe off phase. Prior to the modification portion 510', the resistive force applied to the individual may be gradually increased from a baseline tension (e.g., 0-1 lbs., 1-2 lbs., 2-3 lbs., 3-4 lbs., 4-5 lbs., etc.) to a full rehabilitation tension (e.g., approximately between 30 and 40 lbs.). During the modification portion 510' the resistive force is maintained at full tension. Prior to and/or just after the modification portion 510', the resistive force is gradually decreased back to the base-line. This pattern is repeated on a periodic basis as the individual walks along the ground and/or walking surface.

EXAMPLES

The following example describes a non-limiting embodiment of the present invention, included herein to demonstrate the advantages obtained from aspects of the invention.

Example 1

Gait Rehabilitation for an Individual Having Hemiparesis

Figure 6B:
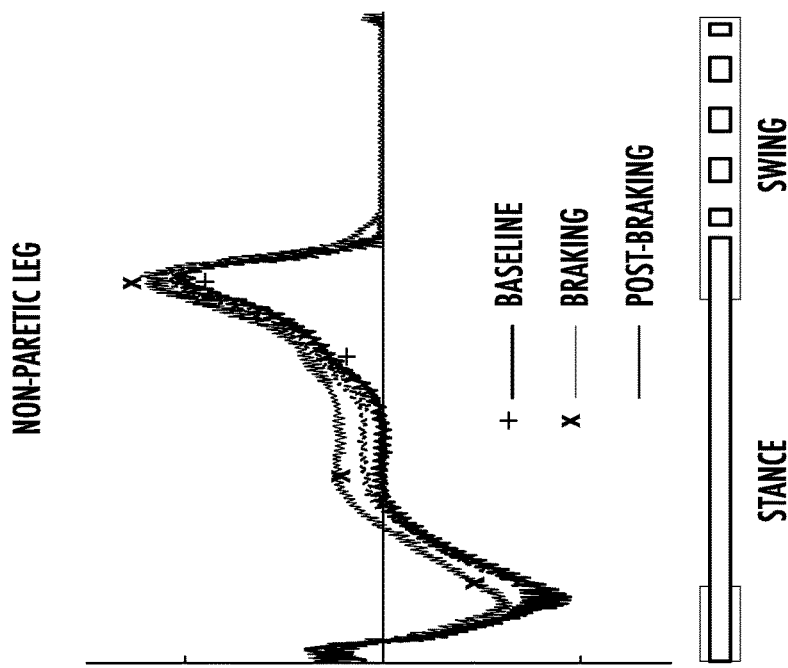
FIG. 6b illustrates the average propulsion force generated by the unaffected leg of an individual before, during, and after the gait rehabilitation sessions of Example 1, which employed aspects of the invention.
Figure 6A:
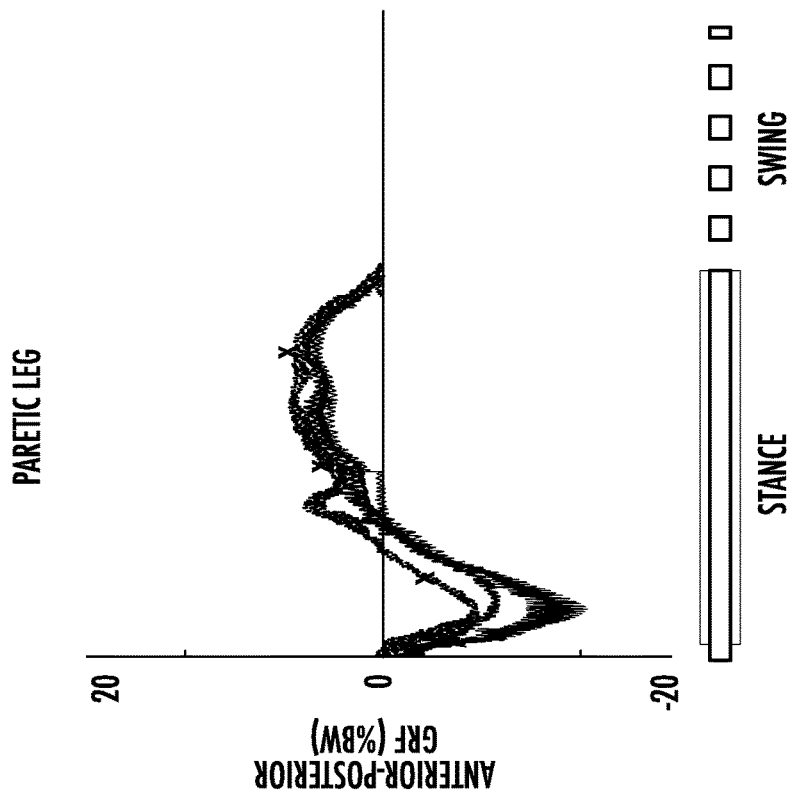
FIG. 6a illustrates the average propulsion force generated by the affected leg of an individual before, during, and after the gait rehabilitation sessions of Example 1, which employed aspects of the invention.

An individual with hemiparesis underwent ten trials of gait rehabilitation using a system in accordance with aspects of the present invention. The individual's propulsion from the affected leg was tested before each session (baseline propulsion), during each session (braking propulsion), and after each session (post-braking propulsion). The braking system 130 applied a braking force, which produced the resistive force to the individual's movement when sensor(s) 110 under the affected foot's great toe sensed pressure, which corresponded to shortly after the affected leg's stance onset, and was released at the onset of the swing phase of the affected leg. The applied resistive force decreased paretic braking force in early stance, affecting anterior, and increased paretic propulsion force in late stance, affecting posterior, compared to the base-line, as illustrated in FIGS. 6a and 6b. FIGS. 6a and 6b show the mean forces in the anterior (negative region of graph) and posterior (positive region of graph) directions for the paretic and non-paretic legs prior to, during, and after the ten gait rehabilitation trials.

Figure 7A:
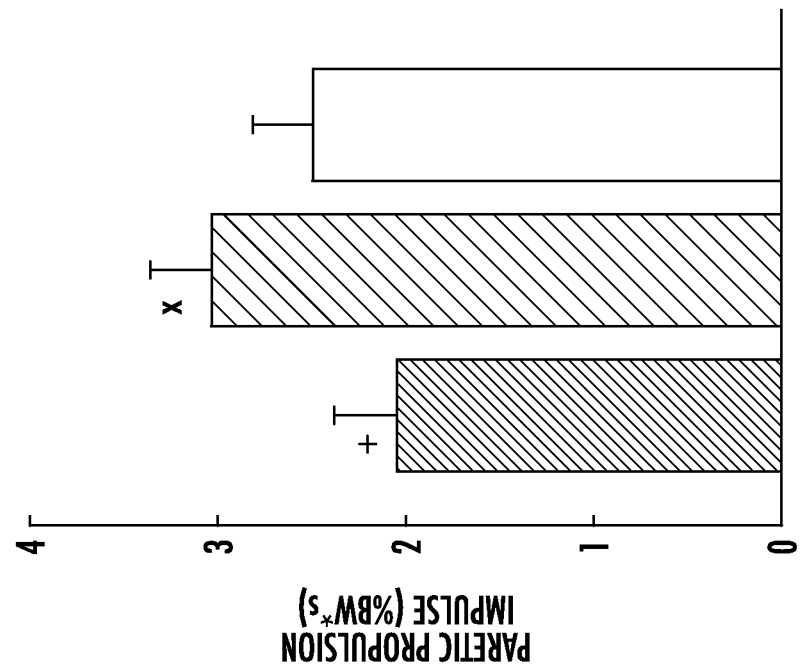
FIG. 7a illustrates the peak paretic propulsion force of the affected leg before, during, and after the gait rehabilitation sessions of Example 1, which employed aspects of the invention.
Figure 7B:
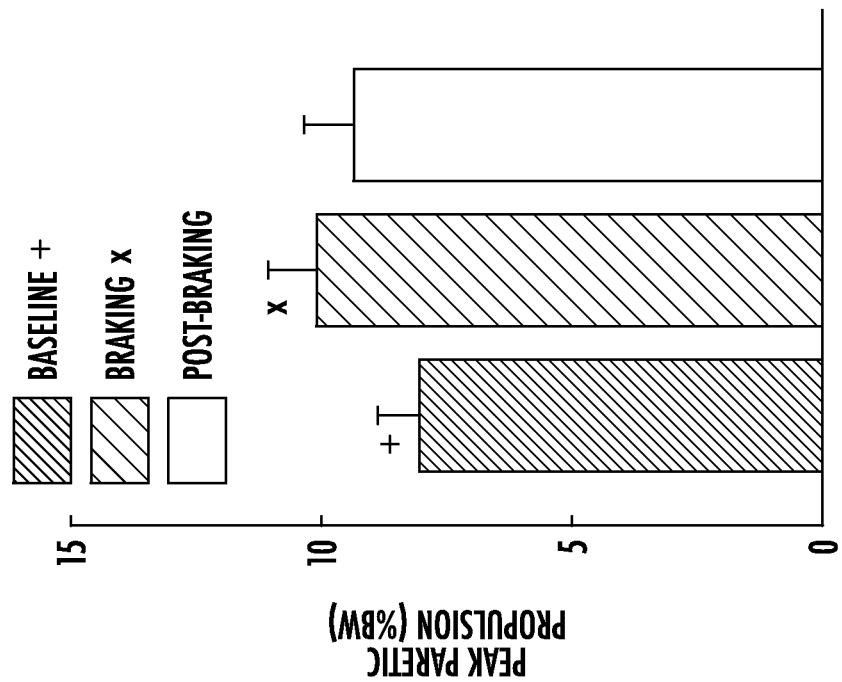
FIG. 7b illustrates the paretic propulsion impulse of the affected leg before, during, and after the gait rehabilitation sessions of Example 1, which employed aspects of the invention.

FIGS. 7a and 7b illustrate the average peak propulsion and the average propulsion impulse of the affected leg prior to, during, and after the ten gait rehabilitation trials. The average peak propulsion and average propulsion impulse increased during the gait rehabilitation trials. Additionally, even after the rehabilitation trials had ended, the average peak propulsion and average propulsion impulse of the affected leg was greater than before the gait rehabilitation trials.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A gait rehabilitation method comprising:
   sensing at least one parameter associated with a gait of an individual, the individual having an affected leg and an unaffected leg;
   determining when the affected leg is in a modification portion of the individual's gait from the sensed at least one parameter; and
   applying a braking force resisting forward movement of the individual during the determined modification portion, wherein the individual wears a harness that is attached to a brake by a tether wound on a spool of the brake and wherein the periodically applying a braking force comprises applying the brake to the spool to increase resistive force needed to unwind the tether from the spool.

2. The method of claim 1, further comprising:
determining when the affected leg is not in the modification portion of the individual's gait from the sensed at least one parameter associated with an individual's gait; and
applying a base-line braking force resisting forward movement of the individual while not in the modification portion.

3. The method of claim 1,
wherein the sensing the at least one parameter comprises sensing force exerted on a walking surface by an affected foot of the affected leg and by an unaffected foot of the unaffected leg; and
wherein the determining when the affected leg is in the modification portion comprises determining when a forward portion of the affected foot is on the walking surface and the unaffected foot is in the air.

4. The method of claim 1,
wherein the sensing the at least one parameter comprises sensing force exerted on a walking surface by an affected foot of the affected leg; and
wherein the determining when the affected leg is in the modification portion comprises determining when a forward portion of the affected foot is on the walking surface.

5. The method of claim 1,
wherein the sensing the at least one parameter comprises sensing force exerted on a walking surface by an unaffected foot of the non-affected leg; and
wherein the determining when the affected leg is in the modification portion comprises determining when unaffected foot is in the air.

6. The method of claim 1, wherein the sensing the at least one parameter comprises sensing movement of at least one of an unaffected foot of the non-affected leg or an affected foot of the affected leg.

7. The method of claim 1, wherein the modification portion comprises the swing phase of the unaffected leg.

8. The method of claim 1, wherein the modification portion comprises at least a portion of the stance phase of the affected leg.

9. A gait rehabilitation method comprising:
sensing at least one parameter associated with a gait of an individual, the individual having an affected leg and an unaffected leg;
determining when the affected leg is in a modification portion of the individual's gait from the sensed at least one parameter; and
applying a braking force resisting forward movement of the individual during the determined modification portion, wherein the individual is supported by a movable structure that enables the individual to exert force with the affected leg on a walking surface, the movable structure having at least one wheel, and wherein the periodically applying a braking force comprises applying the brake to the at least one wheel to increase resistive force needed to move the movable structure.

10. A gait rehabilitation system comprising:
a harness configured for attachment to an individual;
at least one sensor configured to sense at least one parameter associated with gait of an individual, the individual having an affected leg and an unaffected leg; and
a braking system configured for attachment to the harness and in communication with the at least one sensor, the braking system monitoring the at least one sensor to sense the at least one parameter associated with an individual's gait, determining when the affected leg is in a modification portion of the individual's gait from the sensed at least one parameter, and applying a braking force resisting movement of the harness during the determined modification portion, wherein the braking system comprises:
a tether configured for attachment to the harness;
a brake configured to dole out the tether, the brake periodically applying the braking force responsive to a periodic braking signal; and
a processor configured to generate the periodic braking signal responsive to phases of the individual's gait.

11. The system of claim 10, further comprising a support structure supporting the brake and the tether, the support structure having an adjustable height that enables the tether to be doled out at a set height between 30 and 48 inches.

12. The system of claim 10, wherein the brake is configured to provide a maximum resistive force of 35 pounds.

13. The system of claim 10, wherein the brake is configured to apply a resistive force of between 5 and 50 pounds responsive to the periodic braking signal.

14. The system of claim 10, wherein the at least one sensor comprises:
a first set of at least one sensor configured for attachment to an affected foot of the affected leg; and
a second set of at least one sensor configured for attachment to an unaffected foot of the unaffected leg.

15. The system of claim 10, wherein the harness is configured for attachment to a pelvic region of the individual.

16. A gait rehabilitation system comprising:
a harness configured for attachment to an individual;
at least one sensor configured to sense at least one parameter associated with gait of an individual, the individual having an affected leg and an unaffected leg; and
a braking system configured for attachment to the harness and in communication with the at least one sensor, the braking system monitoring the at least one sensor to sense the at least one parameter associated with an individual's gait, determining when the affected leg is in a modification portion of the individual's gait from the sensed at least one parameter, and applying a braking force resisting movement of the harness during the determined modification portion, wherein the braking system comprises: a support structure configured for attachment to the harness;
at least one wheel coupled to the support structure;
a brake configured to apply resistive force to the at least one wheel in response to a periodic braking signal; and
a processor configured to generate the periodic braking signal responsive to phases of the individual's gait.

17. The system of claim 16, wherein the brake is configured to provide a maximum resistive force of 35 pounds.

18. The system of claim 16, wherein the brake is configured to apply a resistive force of between 5 and 50 pounds responsive to the periodic braking signal.

* * * * *